(12) United States Patent
Amaya et al.

(10) Patent No.: US 8,455,038 B2
(45) Date of Patent: Jun. 4, 2013

(54) METHOD FOR PRODUCING ARTIFICIAL BONE AND ARTIFICIAL BONE PRODUCED BY THE METHOD

(75) Inventors: Koichi Amaya, Fukui (JP); Yukinori Urushizaki, Fukui (JP); Hideto Matsubara, Fukui (JP); Nobuo Sasaki, Tokyo (JP); Yuichi Tei, Tokyo (JP)

(73) Assignees: Matsuura Machinery Corp., Fukui-shi, Fukui (JP); The University of Tokyo, Tokyo (JP)

( * ) Notice: Subject to any disclaimer, the term of this patent is extended or adjusted under 35 U.S.C. 154(b) by 285 days.

(21) Appl. No.: 12/946,299

(22) Filed: Nov. 15, 2010

(65) Prior Publication Data

US 2011/0257744 A1    Oct. 20, 2011

(30) Foreign Application Priority Data

Apr. 14, 2010  (JP) .................. 2010-092949

(51) Int. Cl.
 *A61F 2/30* (2006.01)
 *B32B 37/02* (2006.01)
 *B32B 43/00* (2006.01)
 *B23K 15/00* (2006.01)

(52) U.S. Cl.
 USPC ....... 427/2.26; 623/18.11; 264/603; 264/628; 264/678; 156/272.8; 156/281; 219/121.35

(58) Field of Classification Search
 USPC .... 264/1.36, 1.37, 497, 603, 628, 678; 419/8, 419/52; 219/121.6, 121.85, 121.16, 121.17, 219/121.35, 121.65, 121.66; 156/61, 62.2, 156/154, 272.2, 272.8, 281; 427/2.1, 2.24, 427/2.26; 623/16.11–23.76
 See application file for complete search history.

(56) References Cited

U.S. PATENT DOCUMENTS

| | | | | |
|---|---|---|---|---|
| 4,855,102 A | * | 8/1989 | Okada et al. | 419/8 |
| 5,155,324 A | * | 10/1992 | Deckard et al. | 264/497 |
| 5,494,781 A | * | 2/1996 | Ohtani et al. | 430/313 |
| 5,607,607 A | * | 3/1997 | Naiman et al. | 219/121.68 |
| 2007/0142914 A1 | * | 6/2007 | Jones et al. | 623/14.13 |
| 2007/0255418 A1 | * | 11/2007 | Bonnard et al. | 623/18.11 |
| 2008/0004709 A1 | * | 1/2008 | O'Neill et al. | 623/20.35 |
| 2008/0099936 A1 | | 5/2008 | Takinami et al. | |
| 2009/0051082 A1 | * | 2/2009 | Nakamura et al. | 264/497 |

FOREIGN PATENT DOCUMENTS

| | | | | |
|---|---|---|---|---|
| JP | 07008547 A | * | 1/1995 | |
| JP | 2004184606 A | * | 7/2004 | |
| WO | 2007/122783 A1 | | 3/2007 | |
| WO | WO2007122783 A1 | * | 11/2007 | |

* cited by examiner

*Primary Examiner* — Samuel M Heinrich
(74) *Attorney, Agent, or Firm* — Richard M. Goldberg

(57) ABSTRACT

A method for producing an artificial bone capable of accurate molding at a joined part with appropriate strength, in which electromagnetic waves or electron beams are irradiated to a layer of at least type of powder selected from metal biomaterials, ceramics for the artificial bone and plastic resins for the artificial bone based on image data corresponding to a shape of the artificial bone, thereby effecting sintering or melting, and the thus sintered layer or melted and solidified layer is laminated, such that a surface finish step is adopted that inner faces and/or outer faces of both ends and their vicinities configuring the joined part to a human bone part are polished by a rotating tool based on the image data and also irradiation of electromagnetic waves or electron beams at both ends and their vicinities constituting the joined part is set greater than that at other regions.

10 Claims, 5 Drawing Sheets

METHOD FOR PRODUCING ARTIFICIAL BONE AND ARTIFICIAL BONE PRODUCED BY THE METHOD

FIELD OF THE INVENTION

The present invention relates to a method for producing an artificial bone used in surgery of human bodies and others by utilizing a three-dimensional shaping method and an artificial bone based on the method.

DESCRIPTION OF THE RELATED ART

There is a trend that demand for transplantation of an artificial bone for a bone part of a human body where a defect or damage has occurred has increased in line with the development of medical technology.

As shown in Patent Document 1, there has been extensively used a method for producing an artificial bone in which a layer of one or more types of powder selected from metals, resins and ceramics is subjected to laser sintering based on artificial bone image data and the sintered layer is laminated.

Incidentally, it is an ineffability in molding artificial bones that an artificial bone is molded accurately at both ends and their vicinities constituting a joined part to a human bone part.

However, in a conventional method for producing an artificial bone, no particular attention has been paid or no device has been made in this respect. And Patent Document 1 is no exception.

Further, the joined part of an artificial bone is required to be made stronger than other regions in order to prevent fatigue or friction resulting from joining.

However, despite the fact that the above-described laser sintering has been adopted, conventional techniques have failed to provide a configuration in which particular attention is paid to this respect.

PRIOR ART DOCUMENTS

Patent Document

[Patent Document 1] WO2007/122783

SUMMARY OF THE INVENTION

Problems to be Solved by the Invention

An object of the present invention is to provide a method for producing an artificial bone capable of realizing accurate molding at a joined part with appropriate strength and an artificial bone based on the method.

Means for Solving the Problems

In order to attain the above object, a basic configuration of the present invention is made up of the following:

(1) a method for producing an artificial bone in which electromagnetic waves or electron beams are irradiated to a layer of one or more types of powder selected from metal biomaterials, ceramics for an artificial bone and plastic resins for an artificial bone based on image data corresponding to a shape of the artificial bone, thereby effecting sintering or melting, and the thus sintered layer or the thus melted and solidified layer is laminated, and the method for producing an artificial bone in which a surface finish step is adopted in which inner faces and/or outer faces of both ends and their vicinities configuring a joined part to a human bone part are polished by a rotating tool based on the image data, and the step of irradiating irradiates both ends and their vicinities which configure the joined part, by electromagnetic waves or electron beams, with a radiation dose which is set greater than a radiation dose for other regions by either increasing an irradiation dose per unit area, or prolonging an irradiation time in said step of irradiation, to prevent fatigue and friction of said joined part.

(2) an artificial bone which is produced by any one of the above-described methods of (1).

BRIEF DESCRIPTION OF THE DRAWINGS

FIG. 1(a) is a sketch showing a pipe-shaped artificial bone, FIG. 1(b) is a sketch showing a partially pipe-shaped artificial bone, and FIG. 1(c) is a sketch showing a combination of the pipe shaped artificial bone with the partially pipe-shaped artificial bone.

FIG. 2(a) is a cross-sectional view taken in the longitudinal direction, FIG. 2(b) is a cross-sectional view taken in a direction orthogonal to the longitudinal direction (the cross section shown in 2(b) shows a portion taken along the line 2(b)-2(b) in FIG. 2(a)).

FIG. 3(a) is a side elevational view where the peripheral wall is in a meshed state, and FIG. 3(b) is a side elevational view where the peripheral wall is in a pore aggregate state.

FIG. 4(a) is a cross-sectional view showing a sintering step in which electromagnetic waves or electron beams are irradiated, FIG. 4(b) is a cross-sectional view showing a polishing step in which an outer wall of the sintered region is molded, FIG. 4(c) is a cross-sectional view showing a laminating step in which powder is additionally laminated after completion of the polishing step to mold the outer wall, and FIG. 4(d) is a cross-sectional view showing a step in which the inner wall is molded after completion of steps (a), (b) and (c) (the white arrows indicate a state that a rotating tool rotates around and the solid arrows indicate a state that the rotating tool rotates on its own axis).

DESCRIPTION OF THE SYMBOLS

Figure 1A:
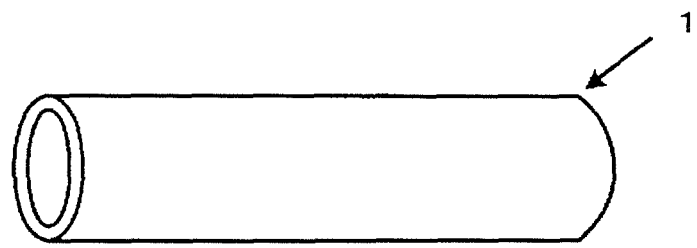
FIGS. 1(a)-1(c) show an artificial bone which is hollow inside.

1: artificial bone
11: end
2: powder
21: sintered region
3: CAD/CAM system
31: CAD system
32: CAM system
4: NC controller
5: apparatus for irradiating electromagnetic waves or electron beams
6: rotating tool
7: electromagnetic waves or electron beams

DETAILED DESCRIPTION

Figure 1B:
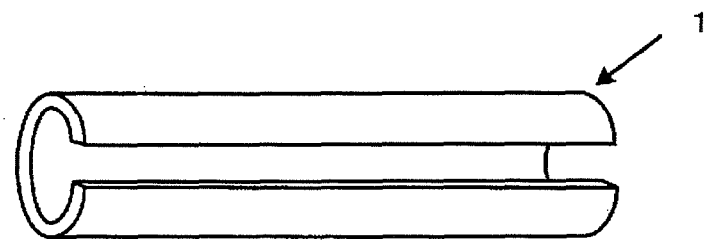
Figure 1C:
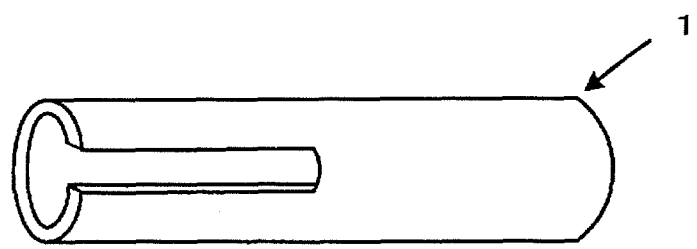
Figure 2A:
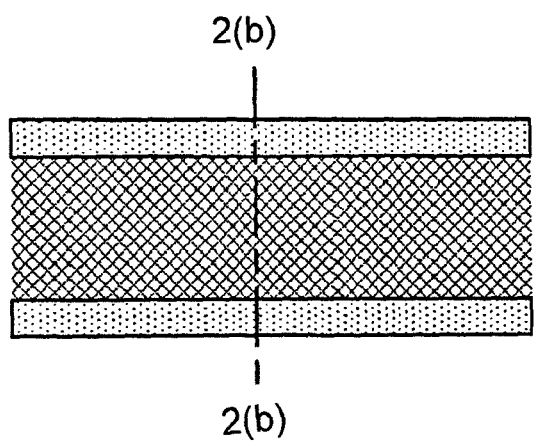
FIGS. 2(a) and 2(b) show an artificial bone in which the interior of a peripheral wall along the longitudinal direction is in a three-dimensional meshed state.
Figure 2B:
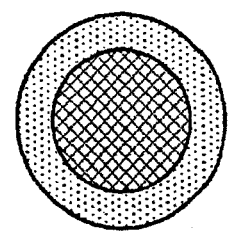

In general, an artificial bone 1 adopts any one of a configuration in which a peripheral wall is made hollow inside as shown in FIGS. 1(a)-1(c) and a configuration in which the peripheral wall is in a meshed state of a three-dimensional structure inside as shown in FIGS. 2(a) and 2(b). (In FIGS. 2(a) and 2(b), the meshed state of the three-dimensional structure is provided all over a region along the longitudinal direction, but a configuration may also be adopted in which a meshed state is provided at a partial region such as both ends and the inside of the peripheral wall besides both ends forming a joined part and positions of their neighborhoods.)

Figure 3A:
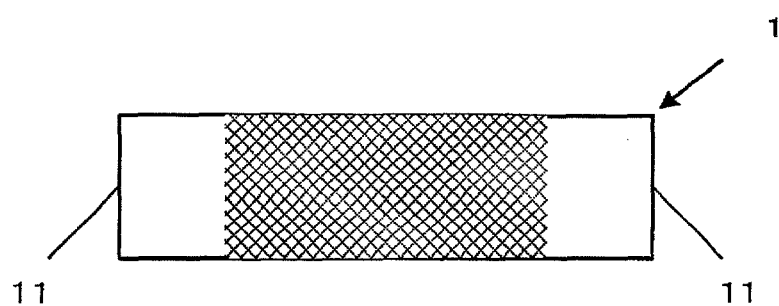
FIGS. 3(a) and 3(b) show an artificial bone which forms a hollow peripheral wall along the longitudinal direction.
Figure 3B:
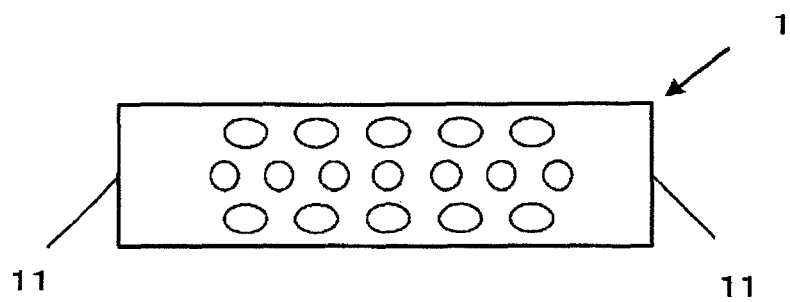

However, the above-described hollow artificial bone includes any one of the pipe shape, the partial pipe shape and the combination of them as shown in FIGS. 1(a), (b) and (c). Further, for the purpose of infiltration of body fluid or allowing body fluid to enter into human tissue, as shown in FIGS. 3(a) and (b), there may be adopted an artificial bone in which a meshed state or a pore aggregate state is provided at all or some regions of a peripheral wall along the longitudinal direction. (In FIGS. 3(a) and (b), there is adopted an artificial bone in which the meshed state or the pore aggregate state is provided at regions other than both ends 11 and their vicinities. However, as a matter of course, it is possible to adopt such a configuration in which any one of these states also covers the both ends 11 and their vicinities.)

In any mode, the artificial bone 1 is joined to a human bone at both ends and their vicinities.

In most cases, the artificial bone 1 is firmly joined to a human bone with a screw in such a manner that the artificial bone 1 is placed outside and the human bone is placed inside. However, as an exception, they can be joined in such a manner that the human bone is placed outside and the artificial bone 1 is placed inside.

Nevertheless, at both ends 11 and their vicinities configuring a joined part, an artificial bone is required to be molded accurately according to the shape of a human bone. Further, for the purpose of avoiding friction and fatigue at the joined part, the joined part is required to be made greater in strength than other regions.

Figure 4A:
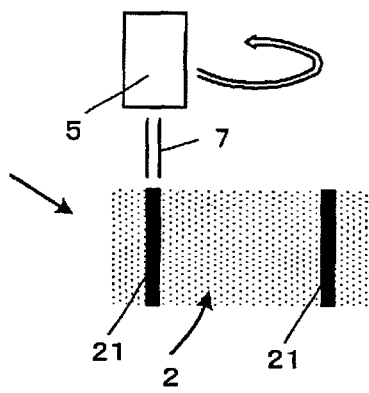
FIGS. 4(a)-4(d) explain that powder is subjected to irradiation by electromagnetic waves or electron beams and polished by a rotating tool, thereby molding an artificial bone.
Figure 4B:
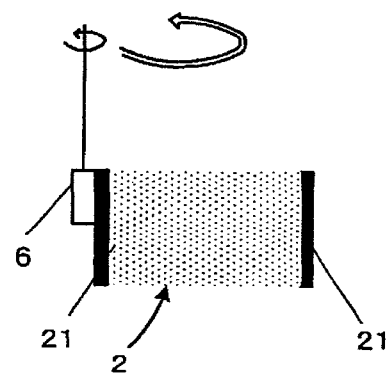
Figure 4C:
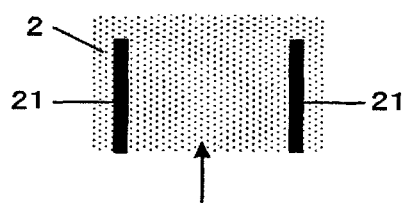
Figure 4D:
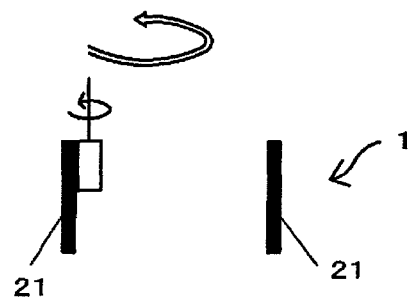

In the previously described basic configuration (1), as shown in FIGS. 4(a) and (c), based on the conventional techniques in which electromagnetic waves or electron beams 7 are irradiated to a layer of one or more types of powder 2 selected from metal biomaterials, ceramics for the artificial bone 1 and plastic resins for the artificial bone 1 to effect sintering and these sintered layers are laminated sequentially, inner faces and/or outer faces of the ends 11 and their vicinities where joining is performed are polished by a rotating tool 6, thereby conducting final molding as shown in FIGS. 4(b) and (d). And, an accurately joined face is provided by this claim.

Then, where a maximum diameter of surface roughness based on the polishing by the rotating tool 6 is to be 10 µm, it is possible to provide an extremely accurate molding and match the needs of medical practices.

There is found no particular trouble resulting from polishing by the rotating tool 6 on inner faces of the ends 11 and their vicinities configuring a joined part. Therefore, in this respect, the basic configuration (1) has technical value.

In an artificial bone 1 where an inner face other than the ends 11 and their vicinities are bent or in an artificial bone 1 where a part further inside the ends 11 and their vicinities is increased in diameter, an ordinary rotating tool 6 smaller in rotating diameter may cause trouble in polishing and molding an inner face.

However, even in these cases, for example, a specially shaped rotating tool having an enlarged rotating diameter at the leading end can be used to overcome the above trouble.

The basic configuration (1) also includes a method for polishing and polishing both inner faces and outer faces of the ends 11 and their vicinities. In this configuration, it is possible not only to provide accurate molding on an inner face to be joined but also to mold a smooth outer face at the end 11 by polishing and polishing, thereby avoiding unnecessary muscle adhesion.

With attention given to the above situation, the basic configuration (1) has adopted a surface finish step in which a region other than a joined part to a human bone part on an outer face of the artificial bone 1 may be polished by the rotating tool 6.

There is such a case that a complicated shape is formed at a leading end of the joined end 11 to a human bone part.

In this case, an embodiment having a polishing step in which leading end faces at both ends are polished by the rotating tool 6 enables accurately shaping the leading end which is complicated in shape, therefore it is favorably applicable.

In normal molding, an outer face is polished and molded by the rotating tool 6 after being sintered by means of electromagnetic waves or electron beams 7 and molded, then laminated further, while in most cases an inner face is polished and molded after completion of polishing and molding of the outer face.

Where the leading end faces of the both ends 11 configuring the joined part are polished by the rotating tool 6, these faces may be polished before or after polishing of the inner face. In most cases, these faces are polished before that.

In the basic configuration (1), irradiation at the ends 11 and their vicinities configuring a joined part is made greater than that at other regions, thereby increasing the strength of the joined part and decreasing the friction and fatigue of the artificial bone 1 at the joined part as much as possible.

To set an irradiation dose at the ends 11 and their vicinities, either one of which the irradiation dose per unit area is increased or the irradiation time is prolonged can be selected.

Where a three-dimensional meshed state or a pore aggregate state is formed at all or some of a peripheral wall along the longitudinal direction as shown in FIGS. 3(a) and (b), in order to maintain necessary strength at a region covering an intermediate portion of the peripheral wall, irradiation dose of electromagnetic waves or electron beams 7 can be set greater than other regions free of the above state.

Figure 5:
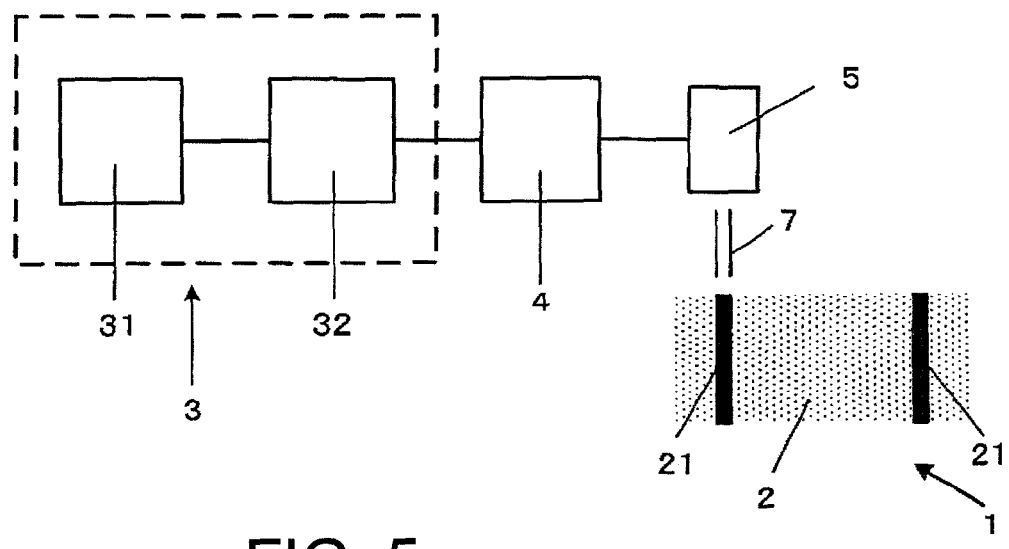
FIG. 5 is a block diagram showing a case where a CAD/CAM system is applied to the present invention.

However, it is also possible that, depending on an area of the meshed region, the number and dimension of a pore aggregate state or an area formed by the aggregate state, such selection can be made that the region concerned is made lower in strength than other regions free of the above state and equal in strength to a human bone.

Where irradiation dose per unit area or irradiation time is changed in the basic configuration (1) and the embodiments shown in FIGS. 3(a) and (b), in most cases, it is changed by such an embodiment that a CAD/CAM system 3 shown in FIG. 5 is adopted, a CAD system 31 is used to set image data corresponding to a shape of the artificial bone 1, and the CAD system 31 or a CAM system 32 is used to set irradiation dose per unit area or irradiation time of electromagnetic waves or electron beams 7 at individual regions of the artificial bone 1.

In the embodiment adopting the CAD/CAM system 3, where electromagnetic waves or electron beams 7 are changed at each of predetermined regions based on the set irradiation dose per unit area or the set irradiation time of the electromagnetic waves or electron beams 7 corresponding to individual regions of the artificial bone 1, the artificial bone 1 at the predetermined region changes in strength. Therefore, appropriate moving velocity and/or rotating velocity where polishing is performed by the rotating tool 6 also change.

In coping with the above-described situation, an embodiment is preferably adopted that in accordance with irradiation dose per unit area or irradiation time of electromagnetic waves or electron beams 7, the CAD system 31 or the CAM system 32 is used to set the moving velocity and/or rotating velocity of the rotating tool 6 as well.

In general, where a spot diameter to be irradiated with electromagnetic waves or electron beams 7 is set less than 100 µm, not only the ends 11 and their vicinities but also other regions can be molded accurately and finely.

Metal biomaterials include Ti-6Al-7Nb, pure Ti, Ti-6Al-4V, Ti-29Nb-13Ta-16Zr, Ti-15Mo-5Zr-3Al, Ti-5Al-5V-5Cr, Ti-15Zr-4Nb-4Ta, Co—Cr alloy, SUS3162, and SUS630. Ceramics for the artificial bone 1 include calcium phosphates (such as hydroxyapatite, α-calcium phosphate and β-calcium phosphate). Plastic resins for the artificial bone 1 preferably include polycarbonate and polyester in terms of strength.

EXAMPLE

Hereinafter, an explanation will be made by referring to an example.

Example

In the example, powder 2 which is metal biomaterial powder or substantially composed of the metal biomaterial powder is adopted as laminated powder 2 at both ends and their vicinities configuring a joined part.

In this example, only metal biomaterial powder or powder substantially composed of the metal biomaterial powder is used at both ends and their vicinities, thus making it possible to maintain necessary strength and also cope with friction and fatigue at the joined part, in addition to the basic configuration (1).

Where powder 2 other than the powder described above in the example is adopted at regions other than the both ends 11 and their vicinities, the powder 2 is switched to the above-described powder to effect laminating at a stage where the both ends 11 and their vicinities are subjected to irradiation. Therefore, in the example, two or more nozzles are preferably used for spraying the powder 2.

Effects of the Invention

Based on the previously described basic configurations (1), (2), (3) and (4), in the case of the artificial bone of the present invention, it is possible to accurately mold the artificial bone at the ends and their vicinities configuring a joined part to a human bone with necessary strength and to exert functions fundamentally required for an artificial bone.

The present invention is widely applicable in producing and using artificial bones.

What is claimed is:

1. A method for producing an artificial bone comprising the steps of:
    irradiating one of electromagnetic waves and electron beams to a layer of at least one type of powder selected from metal biomaterials, ceramics for an artificial bone and plastic resins for an artificial bone, based on image data corresponding to a shape of the artificial bone, thereby effecting at least one of sintering and melting,
    laminating the thus sintered layer or the thus melted and solidified layer,
    a surface finish step of polishing at least one of inner faces and outer faces of both ends and vicinities thereof configuring a joined part to a human bone part by a rotating tool based on the image data, and
    said step of irradiating irradiates said both ends and their vicinities which configure the joined part, by said one of electromagnetic waves and electron beams, with a radiation dose which is set greater than a radiation dose for other regions by one of:
        increasing an irradiation dose per unit area, and
        prolonging an irradiation time in said step of irradiation,
    to prevent fatigue and friction of said joined part.

2. The method for producing an artificial bone according to claim 1, wherein
    a maximum diameter of surface roughness based on the polishing by the rotating tool is 10 µm.

3. The method for producing an artificial bone according to claim 1, further comprising:
    a polishing step for polishing leading end faces of both ends by the rotating tool.

4. The method for producing an artificial bone according to claim 1, further comprising the step of:
    forming one of a meshed region and a pore aggregate region on at least some of a hollow peripheral wall along a longitudinal direction and the formed region is provided with a greater irradiation dose of said one of electromagnetic waves and electron beams than other regions.

5. The method for producing an artificial bone according to claim 1, further comprising the step of:
    using a CAD system to set image data corresponding to a shape of the artificial bone, and
    using one of a CAD system and a CAM system to set at least one of the following:
        irradiation dose per unit area, and
        irradiation time of said one of electromagnetic waves and electron beams
    in the artificial bone.

6. The method for producing an artificial bone according to claim 5, further comprising the step of:
    using the one of the CAD system and the CAM system to set at least one of the moving velocity and rotating velocity of the rotating tool in accordance with at least one of:
        irradiation dose per unit area, and
        irradiation time of said one of electromagnetic waves and electron beams.

7. The method for producing an artificial bone according to claim 1, further comprising the step of:
    forming at least some regions inside a peripheral wall along a longitudinal direction, besides both ends forming joint parts and positions of neighborhoods thereof, into a three dimensional meshed state.

8. The method for producing an artificial bone according to claim 1, further comprising the step of:
    setting a spot diameter to be irradiated with said one of electromagnetic waves and electron beams less than 100 µm.

9. The method for producing an artificial bone according to claim 1, further comprising the step of:
    adopting, as a laminated powder at both ends and vicinities thereof configuring the joined part, one of metal biomaterial powder and powder which is substantially composed of the metal biomaterial powder.

10. An artificial bone produced by the method for producing an artificial bone according to claim 1.

\* \* \* \* \*